United States Patent [19]

Bohn et al.

[11] 4,297,343
[45] Oct. 27, 1981

[54] CONTRACEPTIVE AGENT

[75] Inventors: Hans Bohn; Ernst Weinmann, both of Marburg an der Lahn, Fed. Rep. of Germany

[73] Assignee: Behringwerke Aktiengesellschaft, Marburg an der Lahn, Fed. Rep. of Germany

[21] Appl. No.: 150,572

[22] Filed: May 16, 1980

Related U.S. Application Data

[63] Continuation-in-part of Ser. No. 949,633, Oct. 10, 1978, abandoned.

[30] Foreign Application Priority Data

Oct. 11, 1977 [DE] Fed. Rep. of Germany ....... 2745680

[51] Int. Cl.³ ....................... A61K 39/00; C07G 7/00; A61K 37/00
[52] U.S. Cl. .................................. 424/85; 260/112 B; 260/112 R; 424/177
[58] Field of Search .................... 260/112 B; 424/177, 424/85

[56] References Cited

U.S. PATENT DOCUMENTS

| | | | |
|---|---|---|---|
| 4,191,533 | 3/1980 | Bohn et al. | 260/112 B |
| 4,196,123 | 4/1980 | Rosemberg | 424/177 |
| 4,201,770 | 5/1980 | Stevens | 424/177 |
| 4,217,339 | 8/1980 | Bohn et al. | 260/112 B |

FOREIGN PATENT DOCUMENTS 2616984 10/1977 Fed. Rep. of Germany .

OTHER PUBLICATIONS

"Placental and Pregnancy Proteins" (1979), pp. 290–299.
"The Protein Antigens of Human Placenta as a Basis for the Development of Contraceptive Vaccine", pp. 111–123 (1975).

*Primary Examiner*—Delbert R. Phillips
*Attorney, Agent, or Firm*—Curtis, Morris & Safford

[57] ABSTRACT

What are disclosed are methods for the prevention of pregnancy, or the interruption of pregnancy, in primates by the parenteral administration of a substance which immunologically reacts with the protein $PP_5$ or induces immunologically reactive substances directed against $PP_5$ and pharmaceutical preparations containing such a substance.

2 Claims, No Drawings

CONTRACEPTIVE AGENT

This application is a continuation-in-part application of parent application Ser. No. 949,633 filed Oct. 10, 1978 and now abandoned.

The present invention relates to an agent for the prevention of conception and interruption of pregnancy on an immunological basis.

Contraceptive agents which are active because of immunological reactions have already been described. Thus, attempts have been made to prevent conception in rabbits by antisera against extracts of animal placentas and to induce miscarriages in monkeys and mice. The pregnancy-specific $\beta_1$-glycoprotein is an effective agent for the prevention of conception and for pregnancy interruption in primates (cf. DE-OS No. 2,345,953). An antigen for immunologic fertility control, consisting of protein-like reproduction hormones, is described in DE-OS No. 2,646,023. A contraceptive vaccine having a similar structure is described in DE-OS No. 2,518,546. The last mentioned document in particular considers as a disadvantage the fact that antihormones have an activity which exceeds the reproductiveness, which is undesirable. Even the agents built up on the basis of DE-OS No. 2,345,953 have not always shown the immunological effectiveness necessary for a successful regulation of conception. Thus, attempts have been made to improve the immunogenic activity of the antigens (cf. DE-OS No. 2,543,994). In DE-OS No. 2,646,223 and 2,518,546, too, modified hormone antigens are used.

In addition to the soluble antigens of the human placenta described by H. Bohn in Arch. Gynäk., 212, pages 165–175 (1972), the components of this organ, such as the proteohormones chorionic gonadotropin, placental lactogen and chorionic thyrotropin, are described, as well as the enzymes cystinaminopeptidase, heat-stable alkaline phosphatase and 17-$\beta$-hydroxysteroid-dehydrogenase. The suitability of pregnancy-specific $\beta_1$-glycoprotein as a component of a contraceptive vaccine has already been referred to above; the same applies to the corresponding hormones.

Now, it has been found that substances which are immunologically capable of inducing the formation of antibodies against the placenta-specific glycoprotein $PP_5$ are excellent contraceptives. $PP_5$ is a known placental hormone which can be prepared according to one of the processes of DE-OS No. 2,616,984. It shows an electrophoretic migration in agar gel in the range of the $\beta_1$-globulins. In a polyacrylamide gel it migrates with a relative mobility of 75 in comparison to albumin=100. On the basis of its behavior during gel-filtration on three-dimensionally cross-linked dextran, a molecular weight of about 50,000 was derived for $PP_5$. It is characterized in the most simple way by its immunological reaction with a specific anti-$PP_5$-serum.

Accordingly, the subject of the invention is an agent for the prevention of conception and for the interruption of pregnancy or for inducing an abortion in primates, in particular humans, which contains as essential component an effective amount of a substance which, upon parenteral administration, is capable of reacting immunologically with protein $PP_5$ or which contains immunologically reactive substances which can induce antibodies directed against $PP_5$. Among these are antibodies with immunological determinants directed against $PP_5$, preferably anti-$PP_5$ itself, but also antibodies obtained with derivatives of $PP_5$. Among the substances which are capable of inducing antibodies against $PP_5$, there is to be mentioned in the first instance $PP_5$, furthermore the derivatives thereof. Among the derivatives of $PP_5$ especially those are important which can be prepared by simple reaction of $PP_5$ with a compound which modifies proteins, as well as $PP_5$-conjugates with haptenes, particularly $PP_5$ modified by oxidation, reduction, alkylation, or acylation, $PP_5$ modified by conjugation, with covalent bonding, with a haptene, or $PP_5$ modified by conjugation, with covalent bonding, with a peptide or with another protein.

In such reactions, two basic principles must be taken into consideration. Both lead to a modification of the native structure and, hence, to a denaturation of the protein:

1. Processes for the chemical modification of $PP_5$ with the aid of reagents which cause a modification of chemical groups present.

2. Processes which lead to a chemical modification of $PP_5$ by the introduction of new groups into the molecule or which bring about linkage of the molecule with low molecular weight or high molecular weight compounds.

Processes of this type include those processes by which one or several of the following groups can be modified in proteins: amini, guanidyl, imidazole, indole, aliphatic hydroxyl, amide, thioether, disulfide, sulfhydryl, phenol and carboxyl. For this purpose, a number of reactions is known from the literature for which the reagents metioned hereafter are mainly used under the conditions shown by way of example.

1.1 Oxidation with iodoso-benzoate, porphyridine, ferrocyanide or iodine; a concentration of the oxidizing agent of 0.001–0.01 M, a pH-value of 7, a temperature of 0°–25° C. and a reaction time of 5–30 minutes are generally to be employed. The oxidation with iodine is carried out with iodide in high concentration at a pH-value of 1–7. The oxidation may also be effected with hydrogen peroxide. In this case the preferred conditions are: concentration of the oxidizing agent about 0.005 M, pH-value about 6.6, temperature about 25° C. and reaction time 0.5–40 hours.

1.2 Reduction with cysteine, thioglycolic acid, thioglycol, cyanide or sulfide, preferably under the following conditions: concentration of the reducing agent 0.001–0.1 M, pH-value 7–8, temperature about 25° C. and reaction time 0.4–4 hours.

The reaction conditions may be drawn in detail from the literature. They are reported, for example, by H.S. Olcott and H. Fraenkel-Conrat, Chem. Rev. 41, pages 151 et seq. (1947). In addition, a part of the reagents and process conditions are disclosed by H. E. Schultze and J. F. Heremans, Molecular Biology of Human Proteins (1966) pages 40–41, and in the references cited therein on pages 55 et seq.

With the introduction of new groups into the $PP_5$, derivatives are prepared which are generally designated haptene-compounds from an immunological point of view. According to a recognized definition, a "haptene" is a protein-free substance which can react with an antibody specifically directed against its configuration, but which itself is not capable of forming detectable amounts of antibodies. A haptene produces an immuno-response only in connection with a carrier protein. Most of the haptenes are low molecular weight compounds with a molecular weight of <1000. However, also macro-molecules such, for example, as pneumococci-polysaccharides are considered haptenes. A haptene-protein compound generally leads to the induction of two types of antibodies, whereby specificities against the haptene grouping and against the protein carrier are formed. In the case of $PP_5$, its haptene compounds induce antibodies also against the carrier protein in a homologous system.

Haptenes in the sense of the invention are chemical groups and compounds described as such in literature, in particular aromatic ring systems, steroids, peptides, purines, pyrimidines, penicillin and their derivatives, but also single molecules, for example iodine, and according to a more extended definition given herein of the substances to be bound to the carrier of $PP_5$, also high molecular weight bodies with peptide-, protein- and carbohydrate character, which themselves have antigenic properties.

The processes for the preparation of the derivatives of $PP_5$ according to the above basic principle (2.0) using haptenes are generally applicable reactions for the introduction of protein-modifying chemical groups and of haptenes into protein bodies with formation of a covalent linkage between chemical substances and proteins. In particular, these are reactions described for the modification of individual groups in protein molecules, for example by Olcott and Fraenkel-Conrat and Schultze-Heremans. Examples of such processes are:

2.1 Alkylation with
  iodoacetate, iodoacetamide (0.05–0.1 M, pH 7–8, 0°–25° C., 0.5–2 hours) or
  dinitrofluorobenzene: (0.17 M, pH 7–8, 25° C., 2 hours).

2.2 Acylation with
  ketene (pH 5–8, 0°–25° C., 5–30 minutes),
  acetic anhydride (pH 7–8, 0° C., 30 minutes),
  carbon suboxide (pH 5–8, 0°–25° C., 5–30 minutes),
  azides, benzoyl-, carbobenzoxy- or benzenesulfonyl chloride (pH 7–9, 0°–25° C., 0.5–2 hours),
  nitrous acid (1 M, pH 4, 30 minutes),
  iodine (pH 5–11, 5°–25° C., 0.5–3 hours) (in contradistinction to the above-described oxidation with a smaller amount of iodine and lower iodide concentration),
  formaldehyde (1–2 M, 25° C., at pH 7–8, 1 hour, at pH 11, 10 minutes),
  epoxides (1–2 M, pH 5–6, 1–4 days),
  mustard gas (pH 5–6, 25° C., 0.5–4 hours),
  acid/alcohol (mineral acid in absolute alcohol), (0.01–0.1 M, 0°–25° C., 1–2 days),
  methyldiazoacetate, diazo-acetamide (pH 5 (ester), pH 6, (amide), 0° C.),
  p-chloromercuribenzoate ($10^{-5}$–$10^{-2}$M, pH 7, 25° C., 5–30 minutes),
  diazonium compounds (pH 7–9, 25° C., 30 minutes) or
  o-methylisourea (0.5 M, pH 10.5, 0° C., 3 days).

For some of the above-mentioned groups, the processes are illustrated in more detail hereinafter:

(a) Iodination: (literature: Kabat and Mayer's Experimental Immunochemistry, sec. edition 1961, pages 816–818).

Iodine is reacted as iodinate (alkali metal polyiodide) with tyrosine radicals of the protein, whereby one or two iodine atoms are introduced into the tyrosine molecule and the iodo-protein is formed. In the same manner, the iodine compounds of $PP_5$ are formed.

(b) Diazotization and coupling: (literature: Kabat and Mayer's Experimental Immunochemistry, sec. edition 1961, pages 798–799).

For this purpose a compound with an aromatic amino group, for example arsanilic acid or sulfanilic acid, is diazotized and the diazonium compound is then reacted with the protein. In this reaction mainly tyrosine radicals, but also histidine and lysine radicals, of the protein form a covalent linkage with the aromatic component. According to this process, the diazo-arsanilic acid or the diazobenzene-sulfonic acid compound of the $PP_5$ can be prepared.

(c) Reaction with vinylsulfone compounds: (analogous to the reaction of reactive dyestuffs containing the vinylsulfone group as the reactive component with cellulose or wool).

Aliphatic or aromatic vinylsulfone derivatives and sulfuric acid semi-esters of $\beta$-hydroxyethylsulfones may also be reacted with the amino groups and/or hydroxyl groups of the protein. In such a manner, the haptene compound of $PP_5$ with 1-aminobenzene-4$\beta$-hydroxyethylsulfone-sulfuric acid ester can be obtained.

(d) Reaction with isocyanate and isothiocyanate compounds: (literature: Kabat and Mayer's Experimental Immunochemistry, sec. edition 1961, pages 808–811).

This reaction, which proceeds by way of the free amino groups of the protein, permits, in analogy with the known processes of protein chemistry, the reaction of haptenes having the corresponding chemical grouping also with the $PP_5$.

(e) Dinitrophenylation: (literature: Carsten, M. E. and Eisen, H. N., J.Am. Chem.Soc. 77, 1273 (1955)).

The reaction, carried out in general with dinitrobenzene-sulfonate or dinitrofluorobenzene, leads to the reaction of the free amino groups of the protein with formation of dinitrophenyl derivatives. In this manner, dinitrophenylated $PP_5$ is obtained.

(f) Reaction with mixed anhydrides: (literature: Kabat and Mayer's Experimental Immunochemistry, sec. edition, 1961, pages 813–815).

This process is suitable for linking a number of different haptenes, which must first be converted into a mixed anhydride by acylation, with amino groups of the protein. In addition, by direct reaction of proteins with anhydrides, acid amides of the general formula R—CO—NH-protein, in which R may be any desired haptene, can be prepared in a known manner. With the aid of this reaction, for example the $PP_5$-haptene compound with R=benzyl as the haptene can be prepared.

(g) Reaction with carbodiimides: (literature: Makino, T. et al., Contraception 8 (2), page 133 (1973)).

The carbodiimides of the general formula R—N=C=N—R (R= is any desired organic radical) are suited for linking carboxyl-group-containing haptenes with amino groups of proteins. Also in this case, the compound R—CO—NH-protein is obtained as the reaction product, in which R may be any desired haptene which carries a carboxyl group. With the aid of this reaction, for example the haptene compound of $PP_5$ with cyclohexane-carboxylic acid as the haptene is obtained.

The immunological behavior of $PP_5$ can also be modified according to the invention by linking the glycoprotein with a peptide or protein. This linkage can be effected either covalently or by complex formation. As reaction partners, peptides may be used, for example also those which themselves have a biological function, for example decapeptides such as LRF (luteinizing hormone releasing factor). LRF, for example, can be linked with $PP_5$ in the same manner as is described for the linkage of $PP_5$ with albumin by T. Makino et al. in Contraception 8, 2 (1973), pages 133 et seq. The reaction is based on the carbodiimide activation of the carboxyl groups with carbodiimide compounds.

Another possibility for modifying the immunological behavior of $PP_5$ consists in linking the protein with a second protein substance in the manner described for the linking of enzymes with proteins, wherein $PP_5$ replaces one of the two partners in the reaction. As regards the linkage of the two proteins with each other, a number of processes are known in which individual groups of activating substances such as, carbodiimide, cyanuric chloride, p,p-difluoro-m,m-dinitro-phenylsulfone or glutardialdehyde are used. $PP_5$ can be linked with a series of proteins, for example with the aid of glutaraldehyde in a reaction analogous to that described by S. Avrameas in Immunochemistry 6, (1969), 43–52, for coupling gammaglobulin with peroxydase. According to the invention, $PP_5$ intended as an immunising agent, is preferably linked with a protein substance which itself is active as a component of a vaccine, for example tetanus-toxoid. Other suitable carriers for $PP_5$ are, for example, flagellin, hemocyanine, dextran, killed virus or bacteria, their toxoids, synthetic polypeptides and polynucleotides, and finally polymers which can be biologically degraded such as polylactic acid, polyglycolic acid or collagen.

A preferred embodiment is the reaction product of $PP_5$ with tetanus toxoid, which are linked covalently in a molar ratio of about 10:1 to about 1:1 with the aid of glutardialdehyde.

Furthermore, the invention concerns $PP_5$-derivatives, i.e. protein-modified compounds of $PP_5$, which $PP_5$ is obtained by extraction of human placenta and, for protein modification, subjected to a process for oxidation, reduction, alkylation or acylation of proteins to produce a coavlent linkage between proteins and haptenes or between proteins with one another, and the antisera which can be obtained therefrom.

The reaction products obtained are converted according to known methods into preparations suitable for parenteral injection and, as usual with vaccines, combined, if desired, with stabilizing additives and inorganic or organic immuno-adjuvants, so that they can be used as active immunizing agents for birth control.

As stabilizing additives, substances which improve the stability of the preparations may be used, in particular low molecular weight carbohydrates or albumins or the derivatives thereof such as degraded and re-cross-linked collagen, for exaple the gelatin product which can be obtained under the Trade Mark Haemaccel$^{(R)}$, if desired with other additives such as amino-acid salts, for example sodium glutaminate. The amount of such additives is suitably 0.5% to 5%, optionally up to 10%. The immunizing agent can then be made available in liquid or dry form, suitably in lyophilized form. The latter is then dissolved in water or in a physiologically tolerated medium prior to administration.

As regards the effective dose, two basically different considerations have to be made. If antibody preparations which react directly with $PP_5$ are administered parenterally (passive immunization), in most cases a single injection of about 50 to about 500 mg of globulin containing antibodies against $PP_5$ per kg of body weight is sufficient. With preparations which should induce antibody formation against $PP_5$ (active immunization), single doses of about 0.1 to 50 mg of $PP_5$ or $PP_5$ modified by oxidation, reduction, alkylation, or acylation, of $PP_5$ modified by conjugation, with covalent bonding, with a haptene, or of $PP_5$ modified by conjugation, with covalent bonding, with a peptide or with another protein are used, which are administered suitably 1 to 5 times at intervals of 1 to 3 weeks.

Another object of the invention is the use of the above-described compounds as components of immunizing agents for the prevention of conception and for the induction of abortions.

The following test description shows the success of the passive immunization with $PP_5$-antibodies and active immunization of monkeys with $PP_5$ modified by reaction with diazotized sulfanilic acid or by coupling with tetanus toxoid.

1. Interruption of pregnancy by passive immunization after conception by inducing abortion, preferably in early pregnancy.

A. Preparation of antisera and purification of the antibodies.

40 Rabbits were immunized with human $PP_5$.

For this purpose, the $PP_5$ was dissolved in physiological NaCl solution (concentration 0.06 mg/3 ml) and stirred to form a suspension with addition of aluminum hydroxide. The rabbits were given intravenously injections of 0.05 mg each of protein in 3 ml of suspension per animal on 5 successive days. The animals were then allowed to rest for 10 days. Immunization was then carried out again on 5 successive days with the same amount of antigen, the animals were again allowed to rest for 10 days and finally each time 0.05 mg of the antigen was injected on 5 successive days. After a further period of rest of 7 to 9 days, the animals were bled. After coagulation of the blood, the serum was separated from the coagulum by centrifugation and isolated.

The antibodies were isolated from the serum of the animals by precipitation with $(NH_4)_2SO_4$ (30% w/v) and chromatography with DEAE-cellulose and 0.03 molar phosphate buffer of pH 7. The antibodies migrated unhindered through the column; the other serum proteins remained bound on the DEAE cellulose. The eluate with the antibodies was concentrated to a protein content of 5%, combined with 2.25% of glycine, filtered under sterile conditions, filled into ampules in portions of 5 ml each and lyophilized. Each ampule contained 250 mg of protein.

B. Interruption of pregnancy

On each of three successive days between the 21st and the 27th day of pregnancy, pregnant monkeys of the species Cynomolgus were intravenously given 250 mg portions of the antibody preparation from the rabbits' serum against $PP_5$ dissolved in 5 ml of physiological NaCl solution. 5 out of 7 of the passively immunised animals had an abortion between the 33rd and 48th day of pregnancy. Another monkey (No. 76) had a stillbirth on the 128th day. Only 1 monkey (No. 83) carried to full term. (cf. Table I).

TABLE I

| | Passive immunisation with $PP_5$ | | |
|---|---|---|---|
| Monkey Cynomolgus | Administration of $PP_5$-antibodies Day of pregnancy | Abortion day of pregnancy | Birth |
| 75 | 21–23 | 33 | No |
| 76 | 25–27 | 128 | Yes |
| 77 | 24–26 | 48 | No |
| 78 | 24–26 | 38 | No |
| 81 | 25–27 | 44 | No |
| 82 | 23–25 | 35 | No |
| 83 | 24–26 | — | Yes |

2. Prevention of conception by active immunization with PP$_5$ modified by reaction with diazotized sulfanilic acid or by coupling with tetanus toxoid.

Active immunization is begun at a sufficiently early time before mating to produce a sufficiently high antibody titer which prevents conception either by preventing nidation or by inducing abortion in early pregnancy. This means that immunization must be begun several weeks preferably 2 to 6 weeks, before mating.

Sexually mature female monkeys (Cynomolgus) were immunized, alternately intravenously and subcutaneously, over a period of 6 weeks with a total of 3 mg of a derivative of PP$_5$ in isotonic sodium chloride solution and finely distributed aluminum hydroxide as adjuvant. After immunization, the animals, each time at the time of ovulation, were brought together for 3 days with a male animal capable of fertilisation and the result of the copulation was registered. The female monkeys immunized against PP$_5$ showed a strong inhibition of their reproductiveness, as compared to that of untreated animals. The result obtained with immunized animals was as follows:

Of the 5 monkeys which had been immunized with PP$_5$ modified with diazoted sulfanilic acid and the 6 monkeys which had been immunized with PP$_5$ modified with tetanus toxoid, only 2 became pregnant after the first copulation. Another monkey became pregnant only after the 2nd copulation, 3 after the 3rd and one after the 4th copulation. Of the total of 7 monkeys which had become pregnant, 2 miscarried. There was no apparent difference between the two PP$_5$ modifications.

The control group consisted of 5 animals which are kept in the same manner as the other animals. Instead of the PP$_5$-preparation they were given only an isotonic NaCl solution with finely divided aluminum hydroxide. In this group, 3 monkeys became pregnant after the 1st copulation, another animal after the 2nd and the last after the 4th copulation. All animals gave birth to healthy youngsters.

Instead of PP$_5$ modified with diazotized sulfanilic acid or with tetanus toxoid other derivatives of PP$_5$ obtained by oxidation, reduction, alkylation or acylation can be used with similar results if used in the same fashion at the same dosage rate. They are equivalent.

The following examples serve to illustrate the invention.

EXAMPLE 1

Modification of PP$_5$ with diazotized sulfanilic acid (a) Preparation of the diazonium salt 1 g of sulfanilic acid was dissolved at room temperature in 100 ml of 0.1 N HCl and the whole was placed into ice-water and cooled to 0° C. while stirring. The sulfanilic acid precipitated in the form of a salt. 50 ml of a cold 1% solution of sodium nitrite in water were then added to the suspension dropwise and slowly (in the course of 1 hour), while stirring; termination of the reaction was indicated by blue coloration of potassium-starch paper.

(b) Preparation of the haptene compound

Conjugation of PP$_5$ with the diazotized sulfanilic acid was effected at a weakly alkaline pH value. For this purpose, 20 mg of PP$_5$ were dissolved in 2 ml of a 0.2 M sodium phosphate buffer of pH 8.2 and the solution was cooled to 4° C. Then, 0.11 ml of the solution of the diazonium salt was added and the whole was stirred for 4 hours at 4° C. The pH-value, which should not fall below 8.0, was corrected by the addition of 0.2 N NaOH. The solution was then allowed to stand for 15 hours at 4° C. The modified protein was thoroughly dialyzed against water for several days and finally lyophilized.

A dose of the immunizing agent had the following composition: 0.2 mg of the derivative of PP$_5$ dissolved in 3 ml of isotonic NaCl solution containing 0.05% of Aerosil, 5% of Haemaccel$^{(R)}$ and 0.15 mg of sodium timerfonate as conserving agent.

EXAMPLE 2

Modification of PP$_5$ by coupling with tetanus toxoid

The covalent linkage of PP$_5$ with tetanus toxoid was effected in aqueous solution at pH 5.0 using a water-soluble carbodiimide:

20 mg of PP$_5$ and 60 mg of tetanus toxoid were dissolved in 5.8 ml of water, the pH was adjusted to 5.0 by the addition of 1/10 N hydrochloric acid and 6.6 mg of N-ethyl-N'-(3-dimethyl-aminopropyl)-carbodiimide-HCl were added while stirring. The mixture was then stirred for 3 hours at room temperature (20° C.) and subsequently for 20 hours at +4° C., neutralized and finally dialyzed against an isotonic NaCl solution.

A dose of the immunizing agent had the following composition:

0.5 mg of protein in 3 ml of isotonic NaCl-solution and 1.5 mg of Al(OH)$_3$ (or another immunological adjuvant).

What is claimed is:

1. A method for the passive immunization of a pregnant female primate to induce abortion, which method comprises parenterally administering to said primate an amount, effective for inducing abortion, of antibodies against the placenta-specific glycoprotein PP$_5$.

2. A pharmaceutical preparation for the passive immunization of a pregnant female primate to induce abortion, which preparation comprises an amount, effective for inducing abortion, of antibodies against the placenta-specific glycoprotein PP$_5$ together with a pharmaceutically acceptable parenterally administrable carrier therefor.

* * * * *